United States Patent [19]

Hess et al.

[11] Patent Number: 5,141,518
[45] Date of Patent: Aug. 25, 1992

[54] ANGIOPLASTY CATHETER WITH CLOSE-FITTING GUIDEWIRE AND TUBE

[75] Inventors: Robert L. Hess, Portola Valley; Jeffrey P. Callister, Menlo Park, both of Calif.

[73] Assignee: Progressive Angioplasty Systems, Inc., Menlo Park, Calif.

[21] Appl. No.: 664,652

[22] Filed: Mar. 5, 1991

[51] Int. Cl.⁵ .......................................... A61M 29/02
[52] U.S. Cl. ..................................... 606/194; 604/99
[58] Field of Search ................................ 604/95-103, 604/164, 170; 606/192-194

[56] References Cited

U.S. PATENT DOCUMENTS

| | | | |
|---|---|---|---|
| 3,402,717 | 9/1968 | Doherty | 604/99 X |
| 3,726,283 | 4/1973 | Dye et al. | |
| 3,837,347 | 9/1974 | Tower | |
| 3,890,970 | 6/1975 | Gullen | 604/170 |
| 4,130,119 | 12/1978 | Sessions et al. | |
| 4,444,188 | 4/1984 | Bazell et al. | 604/95 X |
| 4,606,347 | 8/1986 | Fogarty et al. | 606/194 |
| 4,771,778 | 9/1988 | Mar | |
| 4,793,350 | 12/1988 | Mar et al. | |
| 4,813,934 | 3/1989 | Engelson et al. | 604/99 |
| 4,821,722 | 4/1989 | Miller et al. | |
| 4,848,344 | 7/1989 | Sos et al. | 606/194 |
| 4,931,036 | 6/1990 | Kanai et al. | 600/18 |
| 4,932,959 | 6/1990 | Horzewski et al. | 606/194 |
| 4,998,923 | 3/1991 | Samson et al. | 606/194 |
| 5,032,113 | 7/1991 | Burns | 604/96 |

FOREIGN PATENT DOCUMENTS 3408809  9/1985  Fed. Rep. of Germany ...... 606/194

Primary Examiner—John D. Yasko
Assistant Examiner—Adam J. Cermak
Attorney, Agent, or Firm—Burns, Doane, Swecker & Mathis

[57] ABSTRACT

An angioplasty catheter having a tube with a balloon-like member connected to the tube at the distal end thereof and a guidewire removably insertable within the lumen and capable of engaging the end of the catheter within the vicinity of the balloon-like member, the guidewire and the lumen being in close-fitting relationship such that there is insufficient space around the guidewire to allow inflation or deflation of the balloon-like member in a reasonable amount of time with the inserted guidewire.

6 Claims, 2 Drawing Sheets

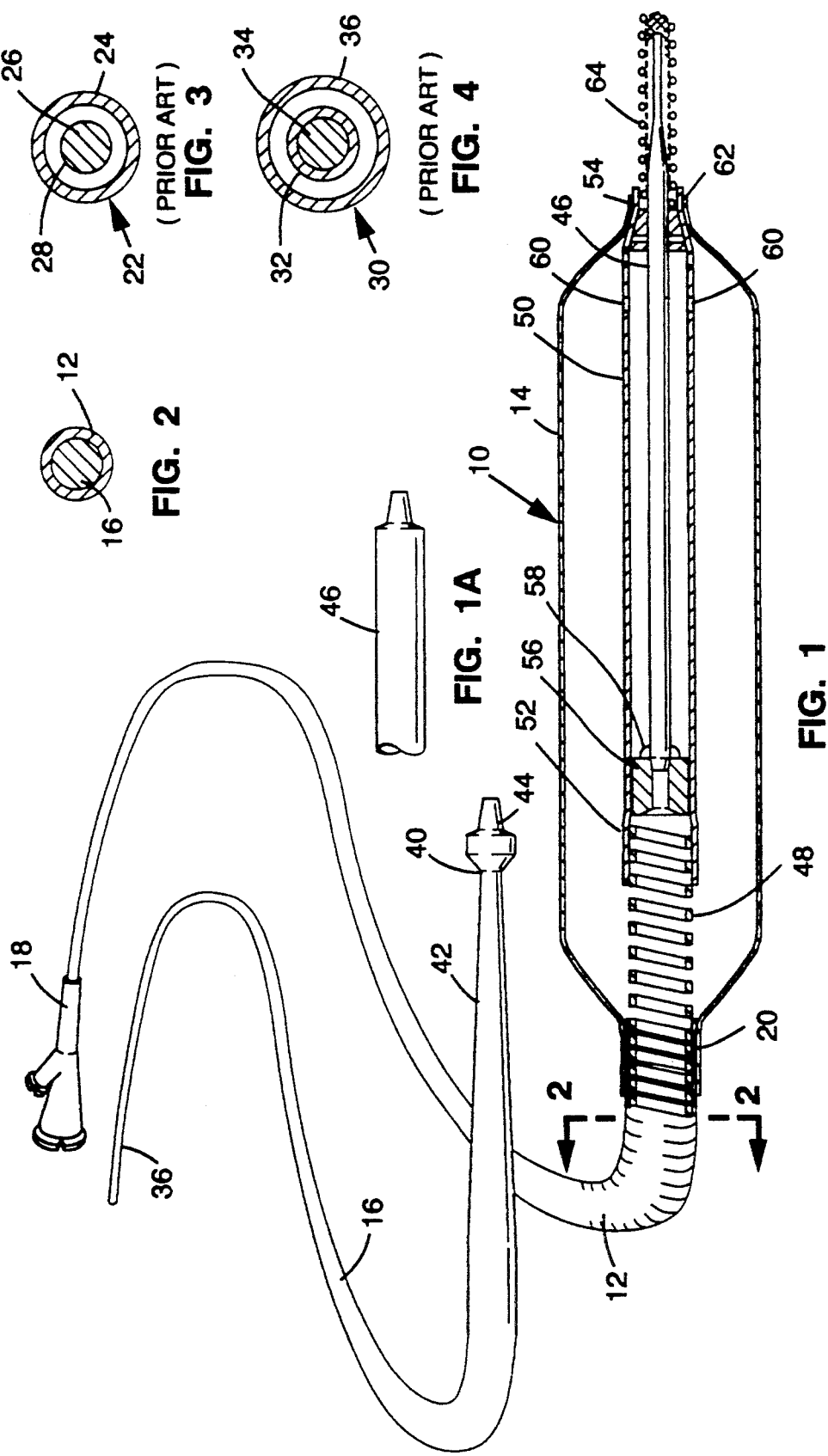

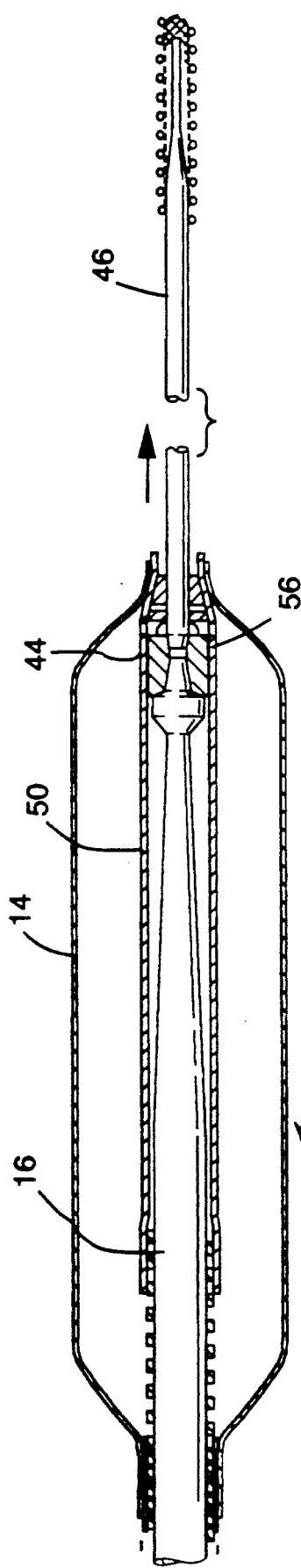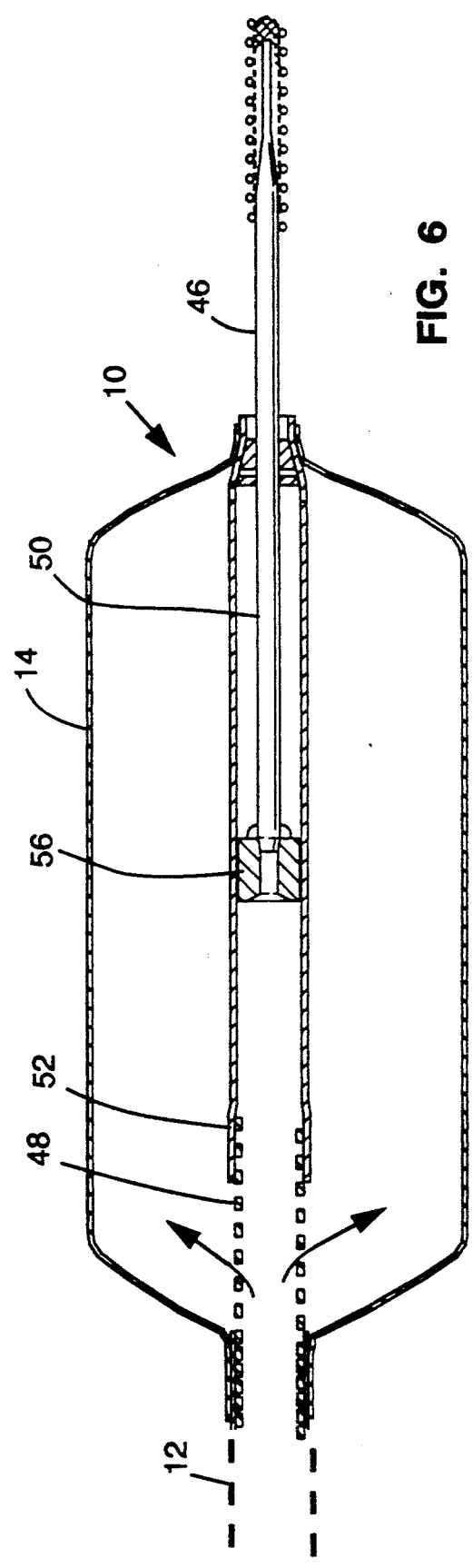

ANGIOPLASTY CATHETER WITH CLOSE-FITTING GUIDEWIRE AND TUBE

BACKGROUND OF THE INVENTION

1. Field of the Invention

The present invention relates to balloon angioplasty catheters and particularly to catheters which provide an inflation tube and a guidewire for pushability and steerability purposes.

2. Description of the Prior Art

There currently are two basic types of balloon angioplasty catheters—"over the wire" ("OTW") and "fixed wire" ("FW").

An OTW catheter provides a tube to accept a guidewire which is moveable and removable and can be extended distal to the distal end of the catheter for steering purposes. An inflation tube is also provided. The advantages of such a catheter are its steerability, column strength (pushability) and the possibility of exchange using the wire. The disadvantage is primarily the catheter's large profile since the device requires two tubes, one concentrically positioned inside the other, to provide an annular passage therebetween for passage of inflation fluid. The wire in such a catheter passes within the inner tube. Unfortunately, the number of components and the annular space increases the overall diameter (profile) of the device and limits its utility.

FW catheters have a single inflation tube around a fixed wire which allows a lower profile. However, this feature is gained at the expense of steerability, pushability and the ability to exchange the wire. Although FW catheters require only one tube and can therefore be smaller in cross-sectional diameter than an OTW catheter, the FW catheter requires space between the inside of the tube and the outside of the fixed wire for the passage of inflation fluid. The larger the diameter of the wire, the larger the diameter of the catheter —thereby limiting the utility of the catheter and also affecting its tractability. FW catheters are also limited because the physical characteristics of the wire, i.e., flexibility, diameter, and taper must be predetermined, thus compromising the FW device's ability to either cross a lesion or to steer the wire with a floppy tip that may be attached to the catheter. In such a situation, the FW catheter must be removed and replaced by another FW catheter, thereby causing further trauma to the blood vessel. These limitations were recognized in U.S. Pat. No. 4,932,959 to Horzewski et al. wherein a catheter is provided with a central tube which slidably receives a guidewire which can be moved back and forth to vary the flexibility of the distal end of the catheter. Unfortunately, in such a device the guidewire is a permanent part of the catheter, and a passage between the wire and the tube must be provided, thereby increasing the overall diameter of the catheter.

As seen from the above discussion, it would be desirable to have a balloon angioplasty catheter having a smaller overall diameter than an FW catheter, yet retaining the variable pushability and steerability of an OTW catheter.

SUMMARY OF THE INVENTION

The purpose of the invention is to provide a balloon angioplasty catheter having the smallest cross-sectional diameter profile possible while providing steerability and pushability. To accomplish this purpose there is provided a catheter which can simply be described as a "balloon on a tube." The instant invention has a tube with a balloon connected to the distal end thereof which accepts a wire, the space between the wire and the tube being sufficient to insert and rotate the wire in the tube yet being insufficient around the inserted wire to allow inflation or deflation of the balloon. The distal tip of the wire is provided with means for engaging and detaching from a rotatable floppy tip assembly to allow steerage of the catheter. The combination of the wire and tube provides exceptional pushability accommodating the insertion of different strength wires wherein stiffness can be varied. The guidewire of the invention is removed during the inflation or deflation of the balloon.

In one aspect of the invention there is provided an angioplasty catheter comprising: a tube, said lumen being elongated and having a proximal end and a distal end; a balloon-like member connected to said lumen at the distal end thereof; and a guidewire removably insertable within said lumen in close-fitting relationship thereto sufficient to allow axial and rotatable movement of the guidewire therein but insufficient to allow adequate inflation or deflation of said balloon.

DESCRIPTION OF THE DRAWING

FIG. 1 is an exploded perspective view of the catheter of the invention including a partially sectioned catheter body and a representative guidewire. FIG. 1A shows the end of another guidewire that can be alternatively inserted into the catheter body.

FIG. 2 is a cross-sectional view of the catheter body with the guidewire inserted therein taken along cross-sectional line 2—2 in FIG. 1.

FIG. 3 is a cross-sectional view similar to FIG. 2 of a prior art fixed wire catheter with a permanent guidewire surrounded by a tube and having an annular space therebetween for passage of balloon inflation fluid.

FIG. 4 is a cross-sectional view similar to FIG. 2 of a prior art over the wire catheter having concentric tubes and a guidewire positioned within the innermost tube. Space is provided between the tubes for passage of balloon inflation fluid.

FIG. 5 is a partial cross-sectional view of the catheter of the subject invention. One of the guidewires has been inserted within the catheter body, and the distal tip of the guidewire has engaged the rotatable floppy tip assembly to steer the catheter.

FIG. 6 is a partial perspective view similar to FIG. 5 wherein the guidewire has been removed and the balloon portion of the catheter has been inflated through the catheter body.

DESCRIPTION OF THE PREFERRED EMBODIMENTS

With continued reference to the drawing, FIG. 1 illustrates an exploded perspective view of the angioplasty catheter 10 of the invention. Catheter 10 includes tube 12, having balloon-like member 14 connected thereto, and guidewire 16 which is removably insertable within tube 12. Tube 12 has a proximal end 18 and a distal end 20. Balloon-like member 14 is connected at distal end 20. A Y-adaptor, or the like, can be attached to proximal end 18 of tube 12 for insertion and removal of guidewire 16 and to allow access to the inside of tube 12 for purposes of inflating balloon-like member 14 once guidewire 16 is removed.

Tube 12 is preferably a wire wound member that is coated to seal the tube for passage of a fluid therein. It is within the scope of the invention to have tube 12 be made of a polymeric material, a coated braid, or other like flexible, sealed conduit. One example is a wire wound member constructed of 0.002 inch by 0.008 inch helically wound Type 304 stainless steel wire coated with 0.0015 inch thickness of polyvinylidene fluoride polymer. It is within the scope of the invention to use other tube constructions of various materials wherein the construction exhibits the appropriate flexibility and sealing. Tube 12 accepts guidewire 16 with such close tolerance that guidewire 16 may be inserted, removed and rotated within tube 12 but with insufficient space to allow inflation or deflation of balloon-like member 14 in a reasonable amount of time with guidewire 16 in place.

FIG. 2 illustrates the close fitting relationship of guidewire 16 within tube 12. As can be seen by comparing FIG. 2 with prior art devices shown in FIGS. 3 and 4, the overall dimension of the subject invention is much smaller.

FIG. 3 illustrates a fixed wire catheter shown generally at 22 having a single inflation tube 24 positioned around a fixed wire 26 and having annular region 28 therebetween for passage of a fluid to inflate a balloon (not shown) that would be positioned at the distal end of such an FW catheter. The term "fixed wire" means that wire 26 is permanently attached to the distal end of the FW catheter and may not be removed; removal would compromise the steerability and pushability of such an FW catheter.

FIG. 4 illustrates an over the wire catheter shown generally at 30 which provides tube 32 to accept guidewire 34 which is moveable and removable and can be extended distal to the distal end (not shown) of the catheter for steering purposes. Inflation tube 36 is also provided. The advantages of OTW catheter 30 over FW catheter 22 are that the OTW catheter is steerable, has high column strength for pushability, and allows for the exchange of guidewire 34. A major disadvantage of the OTW catheter is its large profile. As can be appreciated from FIGS. 2-4, the balloon on a tube construction of the subject invention has a much smaller profile than either OTW catheter 30 or FW catheter 22 and has all of the advantages of OTW catheter 30.

As previously mentioned, catheter 10 may be described as a balloon on a tube in that balloon-like member 14 is attached directly to tube 12. For insertion purposes, guidewire 16 is positioned within tube 12 but is removed for the purpose of inflation. The profile shown in FIG. 2 is therefore the smallest profile of an angioplasty catheter that would benefit from the use of a guidewire.

With reference to FIG. 1, guidewire 16 has a proximal end 38 and a distal end 40. Distal end 40 is shown to be generally tapered at taper 42 to increase the flexibility of guidewire 16. Distal end 40 also includes end portion 44 which engages and manipulates floppy tip wire means 46. It is understood that it is within the scope of the invention for guidewire 16 to have alternative cross-section and/or distal end portions similar to those shown at 42. These alternative guidewires may be varied in material and/or cross-section to alter the flexibility and therefore the steerability of the overall device. FIG. 1a illustrates alternative distal end 40 which is shown as a cylinder having a generally uniform cross-section which for the same material would be less flexible than taper 42.

It can be seen in FIG. 1 that floppy tip wire means 46 is a part of the means for detaching, engaging and rotating the distal end of the catheter to allow steering. Balloon-like member 14 is connected to tube 12 toward distal end 20 of tube 12. Inside balloon-like member 14 the end of tube 12, which preferably comprises a wire wound member, is elongated by stretching the coils 48 of tube 12. Coils 48 are also stripped of their sealing cover such that fluid passing through tube 12 (with guidewire 16 removed) may exit into the interior of balloon-like member 14, both axially and radially, through the spaced coils 48.

Catheter 10 further includes tubular member 50 having proximal end 52 and distal end 54. Proximal end 52 is connected to the distal end of tube 12. The distal end of balloon-like member 14 is connected to tubular member 50 at distal end 54 of tubular member 50. Floppy tip wire means 46 is positioned within tubular member 50 and includes engagement cup 56 which is slidably received within tubular member 50. The engagement cup is connected to floppy tip wire means 46 at 58. At the distal end of catheter 10 a bushing 62 of low friction material such as Teflon ® is positioned about floppy tip wire means 46 beneath the connection of balloon-like member 14 to tubular member 50. Tubular member 50 also includes vent openings 60 to allow fluid that may be contained within tubular member 50 to escape into the interior of balloon-like member 14 as engagement cup 56 moves within tubular member 50.

Engagement cup 56 is complementary in configuration to end portion 44 of guidewire 16 such that end portion 44 engages, rotates and disengages from cup 56. When end portion 44 engages cup 56 and guidewire 16 is extended toward the distal end of catheter 10, end portion 44 moves engagement cup 56 and floppy tip wire means 46 through bushing 62. Although end portion 44 is shown to have a taper to removably engage cup 56, it is within the scope of the invention to use other complementary configurations such as a spline, a barb, a roughened interface or other means to ensure engagement/disengagement. Floppy tip 64 is preferably a wound member of platinum. A safety wire is also attached to secure floppy tip 64.

Although a bushing 62 is shown, it is within the scope of the invention to seal the floppy tip wire means with a high viscosity lubricant such as high molecular weight silica or the like. Other mechanical expedients that will allow movement yet provide sealing are also acceptable.

FIG. 5 illustrates the engagement of end portion 44 of guidewire 16 to engagement cup 56 wherein floppy tip wire means 46 is fully extended through the distal end of catheter 10. The floppy tip wire means 46 may literally be flipped around by the operator much like the bitter end of a line to access an off axis opening. The floppy tip wire means 46 should be sufficiently long to allow such throwing motion when fully extended. In the position shown in FIG. 5, balloon-like member 14 has not been inflated, and the overall stiffness of catheter 10 in the region of balloon-like member 14 is at its greatest to, for example, allow the overall structure to be pushed through a lesion. In practice, balloon-like member 14 would be further compacted onto tubular member 50. This is accomplished by folding deflated balloon-like member 14 on top of itself in overlapping fashion around the circumference of tubular member 50 to reduce the overall profile of catheter 10 in the region of balloon-like member 14. The balloon-like member 14 is not an elastomeric material but rather is a substantially crystalline polymer which is formed into shape by heating, expanding and quenching. Such a balloon-like member is relatively indistensible over a wide pressure range at 37° C. and therefore inflates to a predetermined (as manufactured) size.

FIG. 6 illustrates catheter 10 after the removal of guidewire 16 and the introduction of fluid into the interior of balloon-like member 14 through coils 48 of tube 12. In practice, engagement cup 56 would most likely be positioned near the proximal end 52 of tubular member 50 since engagement cup 56 would be prevented by the end of tube 12 from moving into lumen 12.

From the foregoing detailed description of the embodiments of this invention, it is evident that there may be a number of changes, adaptations and modifications which come within the province of those skilled in the art. However, it is intended that all such variations not departing from the spirit of the invention should be considered to be within the scope thereof as limited solely by the appended claims.

What is claimed is:

1. An angioplasty catheter comprising:
a tube, said tube being elongated having an inside diameter and having a proximal end and a distal end;
a balloon-like member connected to said tube at the distal end thereof and in fluid tight relationship thereto; and
a guidewire having an outside diameter approximately equal to said inside diameter of said tube said tube being a wire wound member which is radially sealed along the majority of the length thereof, said guidewire removably insertable within said tube in close-fitting relationship thereto sufficient to allow axial and rotatable movement of the guidewire therein but insufficient to allow adequate inflation or deflation of said balloon-like member.

2. A catheter as in claim 1 wherein said winding is elongated at the distal end of said tube and is unsealed to allow communication with the inside of said tube both axially and radially through the coils of said tube, said balloon-like member enveloping said elongated and unsealed portion of said tube.

3. A catheter as in claim 2 further including tip control means within said balloon-like member, said tip control means being an elongated tubular member connected at one end of said tubular member to the distal end of said tube, said balloon-like member connected at one end thereof to said tube along a sealed portion thereof remote from the distal end of said tube, the other end of said balloon-like member connected to the other end of said tubular member, said balloon-like member also enveloping said tubular member.

4. A catheter as in claim 3 wherein said tip control means further includes floppy tip wire means positioned within said tubular member, one end of said floppy tip wire means having an engagement cup means positioned within said tubular member closest to said tube and the other end of said floppy tip wire means extending axially beyond said tubular member and said balloon-like member, said engagement means being complementary in configuration to the distal end of said guidewire to allow removable connection with the distal end of said guidewire to allow limited axial movement of said guidewire and said floppy tip wire means together.

5. A catheter as in claim 4 further including a platinum floppy tip connected to said floppy tip wire means outside of said balloon-like member.

6. A catheter as in claim 4 wherein said floppy tip wire means further includes a bushing around said floppy tip wire means, said bushing made of low friction material, said bushing aligning and providing a fluid-type seal about said floppy tip wire means, said tubular member having vent means near the distal end thereof communicating the inside of said tubular member with the inside of said balloon-like member.

* * * * *

UNITED STATES PATENT AND TRADEMARK OFFICE
CERTIFICATE OF CORRECTION

PATENT NO. : 5,141,518
DATED : August 25, 1992
INVENTOR(S) : Hess, et al.

It is certified that error appears in the above-identified patent and that said Letters Patent is hereby corrected as shown below:

In the "Abstract" lines 4 and 6, delete "lumen" and insert --tube-- therefor;

Column 2, lines 15, 17 and 19, delete "lumen" and insert --tube-- therefor;

Column 5, line 11, delete "lumen" and insert --tube-- therefor.

Signed and Sealed this

Seventh Day of December, 1993

*Attest:*

BRUCE LEHMAN

*Attesting Officer*  *Commissioner of Patents and Trademarks*